United States Patent
Efrati et al.

(10) Patent No.: US 9,688,585 B2
(45) Date of Patent: Jun. 27, 2017

(54) LIGHTWEIGHT ASSEMBLABLE APPLIANCE AND RESPECTIVE METHOD FOR PRODUCTION OF BIOGAS AND LIQUID FERTILIZER

(71) Applicant: ECOGAS ISRAEL LTD, Moshav Sde Zvi (IL)

(72) Inventors: Oshik Moshe Efrati, Michmoret (IL); Yair Teller, Har Amasa (IL); Erez Lanzer, Moshav Sde Zvi (IL); Yariv Miller, Hadera (IL); Tal Eilon, Kibutz Kfar Aza (IL); Shoham Zak, Givat Ela (IL)

(73) Assignee: ECOGAS ISRAEL LTD, Moshav Sde Zvi (IL)

( * ) Notice: Subject to any disclaimer, the term of this patent is extended or adjusted under 35 U.S.C. 154(b) by 0 days.

(21) Appl. No.: 14/899,620

(22) PCT Filed: Dec. 19, 2013

(86) PCT No.: PCT/IB2013/061160
§ 371 (c)(1),
(2) Date: Dec. 18, 2015

(87) PCT Pub. No.: WO2014/203047
PCT Pub. Date: Dec. 24, 2014

(65) Prior Publication Data
US 2016/0137562 A1 May 19, 2016

Related U.S. Application Data

(60) Provisional application No. 61/916,246, filed on Dec. 15, 2013.

(30) Foreign Application Priority Data

Jun. 18, 2013 (WO) .................. PCT/IB2013/001272

(51) Int. Cl.
*C12M 1/107* (2006.01)
*C05F 17/02* (2006.01)
(Continued)

(52) U.S. Cl.
CPC ............ *C05F 17/0258* (2013.01); *C05F 9/02* (2013.01); *C05F 17/0018* (2013.01);
(Continued)

(58) Field of Classification Search
CPC ...... C12M 21/04; C12M 23/14; C12M 23/26; C12M 23/36; C12M 23/44; C12M 23/46; C12M 23/48; C12M 23/54
See application file for complete search history.

(56) References Cited

U.S. PATENT DOCUMENTS 4,100,023 A * 7/1978 McDonald ................ C02F 3/28
435/167
4,169,048 A 9/1979 Albers, Sr.
(Continued)

FOREIGN PATENT DOCUMENTS

CA    2731439 A1    8/2012
CN    101 460 413 B    5/2007
(Continued)

OTHER PUBLICATIONS

English language machine translation of DE 8304514U1 (Apr. 1986), pp. 1-13.*
(Continued)

*Primary Examiner* — William H Beisner
(74) *Attorney, Agent, or Firm* — Mark David Torche; Patwrite LLC (57) ABSTRACT

A system and method of recycling organic waste into biogas, implementing an anaerobic digestion processes, is disclosed. The system includes structural scaffolding and a pliable collapsible anaerobic digester. The aerobic digester includes
(Continued)

at least one suspension tab, rendering the anaerobic digester suspendable from the structural scaffolding. A respective kit-of-parts is disclosed for assembling the aforementioned system.

36 Claims, 8 Drawing Sheets

(51) Int. Cl.
    *C12M 1/00*     (2006.01)
    *C12M 3/00*     (2006.01)
    *C12P 5/02*     (2006.01)
    *C05F 17/00*     (2006.01)
    *C05F 9/02*     (2006.01)

(52) U.S. Cl.
    CPC ...... *C05F 17/0027* (2013.01); *C05F 17/0063* (2013.01); *C05F 17/0205* (2013.01); *C05F 17/0211* (2013.01); *C12M 21/04* (2013.01); *C12M 23/14* (2013.01); *C12M 23/26* (2013.01); *C12M 23/36* (2013.01); *C12M 23/38* (2013.01); *C12M 23/46* (2013.01); *C12M 23/48* (2013.01); *C12M 23/52* (2013.01); *C12M 23/54* (2013.01); *C12M 29/00* (2013.01); *C12M 47/18* (2013.01); *C12P 5/023* (2013.01); *Y02E 50/343* (2013.01); *Y02P 20/145* (2015.11); *Y02W 10/37* (2015.05); *Y02W 30/43* (2015.05); *Y02W 30/47* (2015.05)

(56) References Cited

U.S. PATENT DOCUMENTS

| | | | |
|---|---|---|---|
| 4,632,692 A | | 12/1986 | Lebesgue et al. |
| 5,316,387 A | * | 5/1994 | Polett ................ B65D 88/1631 |
| | | | 383/119 |
| 5,651,890 A | * | 7/1997 | Trost ........................ C02F 3/28 |
| | | | 210/603 |
| 6,375,838 B1 | | 4/2002 | Malige et al. |
| 7,186,339 B1 | | 3/2007 | Roos |
| 2004/0045899 A1 | | 3/2004 | Humphrey |
| 2007/0191527 A1 | | 8/2007 | Mallikarjuna et al. |
| 2008/0131960 A1 | * | 6/2008 | Belongia ................ C12M 23/26 |
| | | | 435/296.1 |

FOREIGN PATENT DOCUMENTS

| | | | | |
|---|---|---|---|---|
| CN | 201400673 Y | | 2/2010 | |
| CN | 101337737 B | | 8/2010 | |
| CN | 202 022 927 U | | 11/2011 | |
| CN | 102 518 599 A | | 6/2012 | |
| CN | 202 610 224 U | | 12/2012 | |
| DE | 8304514 U1 | * | 4/1986 | ........... C12M 21/04 |
| EP | 0033724 A2 | | 8/1981 | |
| FR | 2983848 A1 | | 6/2013 | |
| GB | 2162195 A | | 1/1986 | |
| WO | 02062497 A1 | | 8/2002 | |
| WO | 2010100309 A1 | | 9/2010 | |

OTHER PUBLICATIONS http://www.build-a-biogas-plant.com/biogas-kits/.
www.build-a-biogas-plant.com/biogas-kits/.
Karthik Rajendran et al: "Household Biogas Digesters-A Review" Energies, vol. 5, No. 12, Dec. 8, 2012 (Dec. 8, 2012) pp. 2911-2942, XP055271569,CH ISSN: 1996-1073, DOI: 10.3390/en5082911 p. 2923.

* cited by examiner

LIGHTWEIGHT ASSEMBLABLE APPLIANCE AND RESPECTIVE METHOD FOR PRODUCTION OF BIOGAS AND LIQUID FERTILIZER

TECHNICAL FIELD

In general, the present invention pertains to systems and methods of recycling organic waste and utilizing the products thereof. In particular, the invention relates to a system, optionally forming an autonomic standalone unit, for recycling organic waste, implementing essentially anaerobic digestion processes.

BACKGROUND ART

Household organic waste makes up a considerable percentage of total waste. This waste is typically thrown out with the rest of the garbage, requiring transport and space in dumps. Such waste is occasionally used for the purposes of producing compost, saving the transport and space requirements, as well as providing a source of rich soil. Hence improved system and methods for combined biogas and fertilizer production from such waste organic waste shall entail an environmental benefit.

Previous attempts include method and device, disclosed in international patent application PCT/ES2010/070120, publication number WO/2010/100309, used for the recycling and exploitation of biodegradable domestic waste produced in the dwellings of a community, by means of prefabricated biogas-production plants, in order to produce electricity and fertilizer and to heat water. The waste is ground in a grinder provided in the kitchen sinks and is conveyed, by means of a network separate from the sewage network, to a biogas-production plant formed by digesters, where biogas is produced by means of anaerobic digestion.

Yet previous attempts include method and device, disclosed in US2010/233778, for generating biogas from organic materials having a biogas reactor which has a charging chamber for being charged with the organic materials and a backflow channel for an at least partial discharge of the organic materials from the biogas reactor. According to US2010/233778 the biogas reactor in addition has at least one intermediate chamber, the charging chambers of which form at least one intermediate chamber and the backflow channel form in this sequence sections of a flow path through which flow can pass in only one direction for the organic materials, two sequentially following sections respectively forming a rising flow path in one case and a falling flow path in the other.

It is further believed that the current state of the art is represented by U.S. Pat. No. 4,565,552 and U.S. Pat. No. 7,186,339; European patent EP0045114; Chinese patents and utility models CN201575295, CN201400673, CN201915092 and CN202576409, as well as by international patent applications having publication numbers WO2011133023 and WO2012153256.

BRIEF SUMMARY

In accordance with one aspect of invention there is provided a system, forming an autonomic standalone unit, for recycling organic waste into biogas and liquid fertilizer.

In accordance with another aspect of invention there is provided a method of producing biogas and liquid fertilizer by the means of system, implementing essentially anaerobic digestion processes.

In accordance with yet another aspect of invention there are provided systems and methods of sustaining fluent operation of the aforementioned system, as an autonomic standalone unit.

In accordance with still another aspect of invention there are provided systems and methods allowing convenient utilization of biogas and liquid fertilizer products resulting the digestion process.

In accordance with yet still another aspect of invention there is provided a lightweight appliance, for recycling organic waste into biogas and liquid fertilizer, assemblable from a compact kit-of-parts, convenient for shipment and deployment.

DEFINITIONS

The term assemblable, as referred to herein, is to be construed inter alia as capable of being assembled and deployed, rather readily and promptly, from a kit of parts.

The term assemblable, as referred to herein, is to be construed as including disassemblable or capable of being relatively easily dismantled or disassembled for relocation and/or redeployment.

The term assemblable, as referred to herein, is to be construed, inter alia, as providable or capable of being provided in a compact form as well as in dismantled or disassembled form.

Terms and expressions "in a compact form" and alike are to be construed as assuming a final construction size substantially larger than the size of assumed by aforesaid compact form.

The term suspendable, as referred to herein, is to be construed as capable of being suspended and/or hanged from a support structure.

DESCRIPTION OF THE DRAWINGS

The present invention will be understood and appreciated more comprehensively from the following detailed description taken in conjunction with the appended drawings in which.

While the invention is susceptible to various modifications and alternative forms, specific embodiments thereof have been shown merely by way of example in the drawings. The drawings are not necessarily complete and components are not essentially to scale; emphasis instead being placed upon clearly illustrating the principles underlying the present invention.

DETAILED DISCLOSURE OF EMBODIMENTS

Illustrative embodiments of the invention are described below. In the interest of clarity, not all features of actual implementation are described in this specification. It will of course be appreciated that in the development of any such actual embodiment, numerous implementation-specific decisions must be made to achieve the developers' specific goals, such as compliance with technology- or business-related constraints, which may vary from one implementation to another. Moreover, it will be appreciated that the effort of such a development might be complex and time-consuming, but would nevertheless be a routine undertaking for those of ordinary skill in the art having the benefit of this disclosure.

In accordance with some embodiments of the present invention, reference is now made to FIG. 1A to 5, showing system 10, as well as structural details of the components thereof. System 10 forms an autonomic standalone unit, utilized for recycling organic waste into biogas and liquid fertilizer. Preferably system 10 is assemblable with a minimal set of hand tools. System 10 is yet preferably assemblable by hand.

As shown particularly in FIGS. 1A-B and 2A-B, system 10 is covered by exterior enclosure 12. In an embodiment, exterior enclosure 12 is connected to and exterior to structural scaffolding 42. Exterior enclosure 12 typically comprises a transparent or translucent material, adapted to sustain a greenhouse effect, by capturing some of the solar energy. It is noted that system 10 employs essentially anaerobic and non-exothermic digestion processes. Therefore an external source of heat is preferably employed for sustaining an effective and fluent continuation of the anaerobic digestion processes, facilitated by the greenhouse effect of exterior enclosure 12. In some preferred embodiments exterior enclosure 12 comprising at least one detachable or partially detachable portion (not shown), configured to allow easy access to internal components of system 10, for maintenance and repair thereof. In some embodiments, an entirely or partially detachable portion of exterior enclosure 12 is fastened to the exterior enclosure 42 by a means of zip fastener, otherwise known as a clasp locker, hook and loop fastener, such as fastener commercialized under the trademark of Velcro®, or similar means.

Figure 1A:
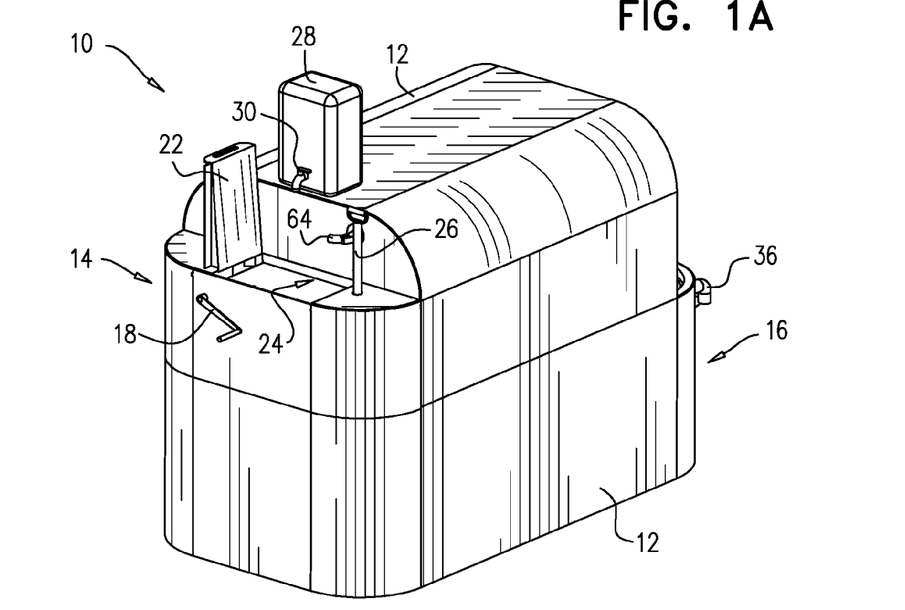
FIG. 1A is a front perspective view of a preferred embodiment of a system for production of biogas and liquid fertilizer.
Figure 1B:
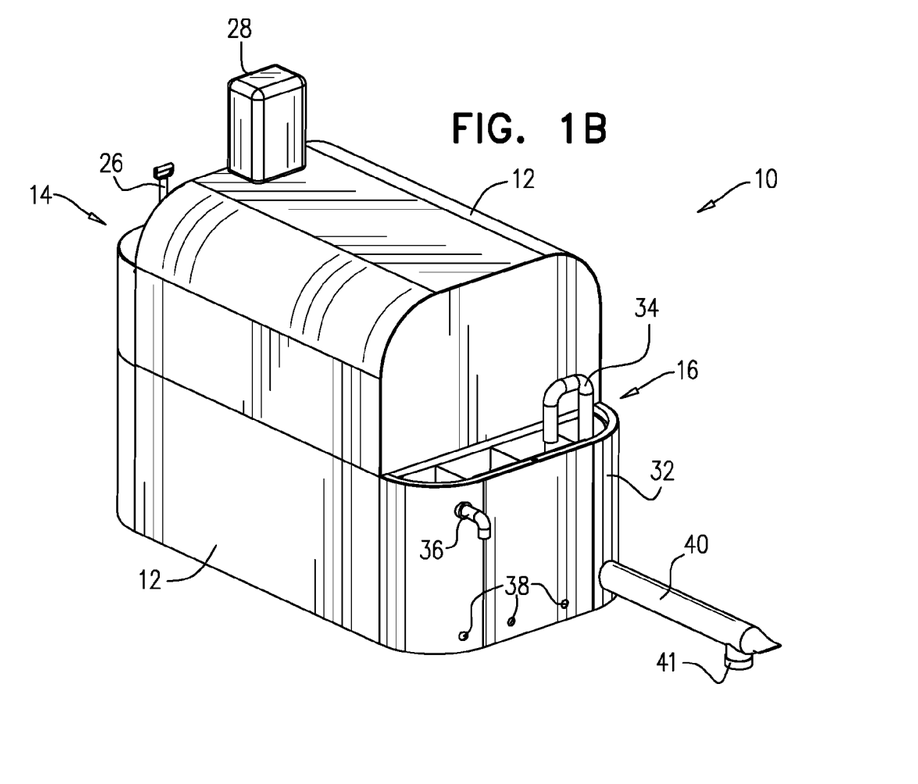
FIG. 1B is a back perspective view of a preferred embodiment of the system for production of biogas and liquid fertilizer.
Figure 1C:
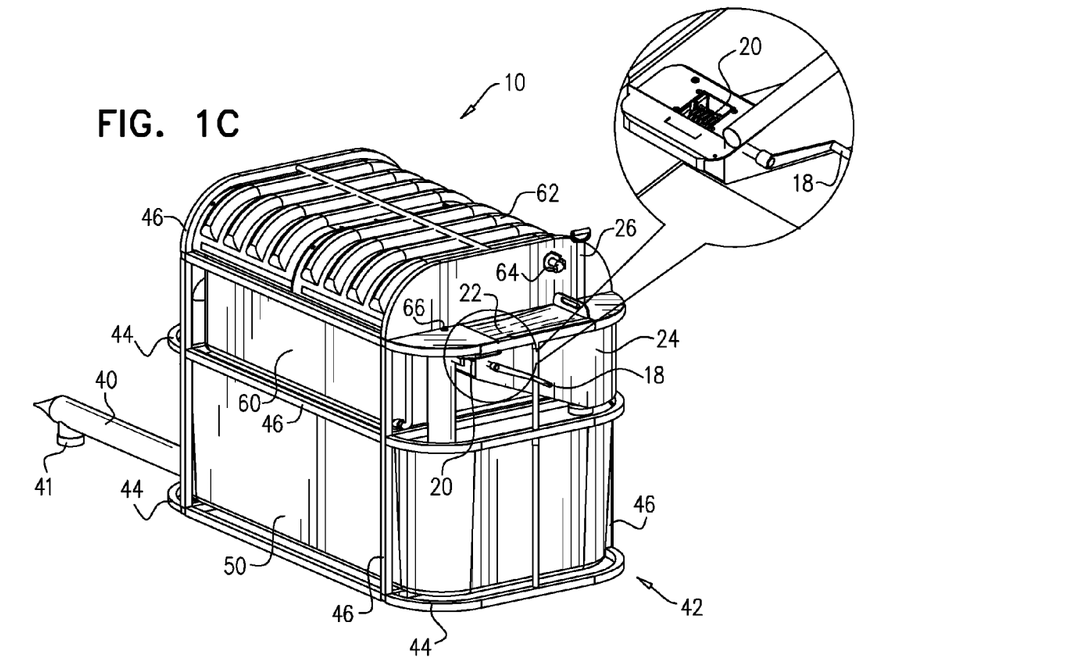
FIG. 1C is a front perspective view of a preferred embodiment of the system, without the exterior enclosure, showing the interior components thereof.
Figure 1D:
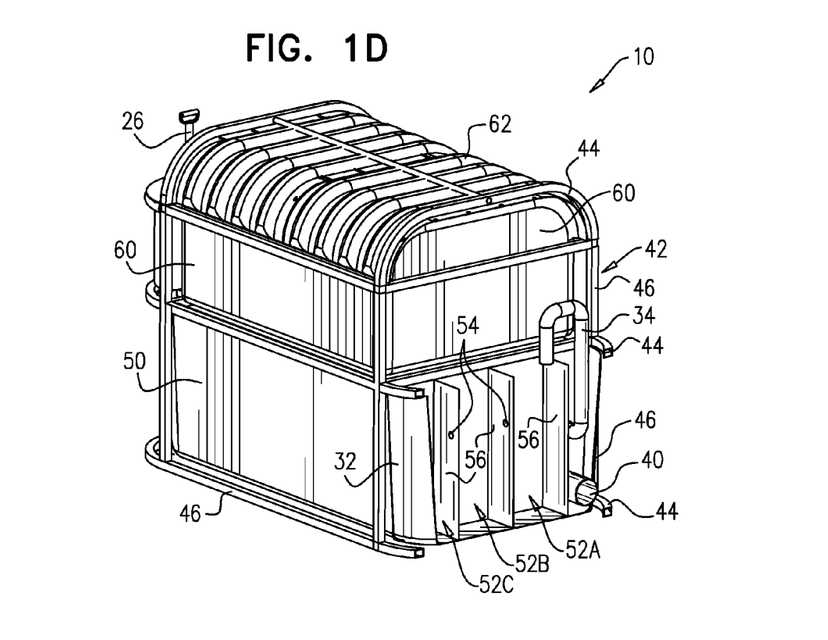
FIG. 1D is a perspective cross-sectional view of the back portion of a preferred embodiment of the system, without the exterior enclosure.

Referring particularly to FIG. 1C-D, system 10 comprises anterior portion 14 and posterior portion 16. Anterior portion 14 and accommodates feeding sub-assembly comprising sink 24, grinder 20 and sink cover 22, as well as optionally fluid canister 28, or a fluid supply hose (not shown) disposed on top of sink 24, furnished with tap 30.

Grinder 20 shown in FIG. 1C is typically driven either manually, for instance by the means of handle 18, or by a motor (not shown) connected to a power source. Sink cover 22 preferably comprises a sloped or slanted structure, adapted for conveniently feeding-in organic waste into grinder 20. In some preferred embodiments sink cover 22 is pivotally attached to the edge of sink 24 adjacent to grinder 20, thereby allowing sink cover 24 to assume a horizontal and vertical conformations. In horizontal conformation, the sloped or slanted structure sink cover 22 facilitates convenient feeding-in of organic waste into grinder 20; whereas in vertical conformation sink cover 22 provides for access to the interior lumen of sink 24 allowing manually manipulating the contents of sink 24 towards the outlet thereof.

The aforementioned feeding sub-assembly is employed for processing an organic waste into a semiliquid mixture or slurry of ground organic matter and fluid, by grinding the organic waste (e.g. by grinder 20) and mixing the ground organic with fluid, controllably supplied via tap 30. The semiliquid mixture or slurry of ground organic matter and fluid is then fed into pliable collapsible anaerobic digester 50 through inlet pipe 27, which is connected to the outlet of sink 24. In one embodiment, anaerobic digester 50 is fed with fluids in a non-limiting manner including: water, grey water and slurry overflow fluid.

In some embodiments, alternative or additional sink (not shown), other than of sink 24, is used for animal droppings which are optionally utilized by system 10, typically without grinding. In such cases, there is a soaking treatment, in the alternative or additional sink or in a separate container.

Figure 3A:
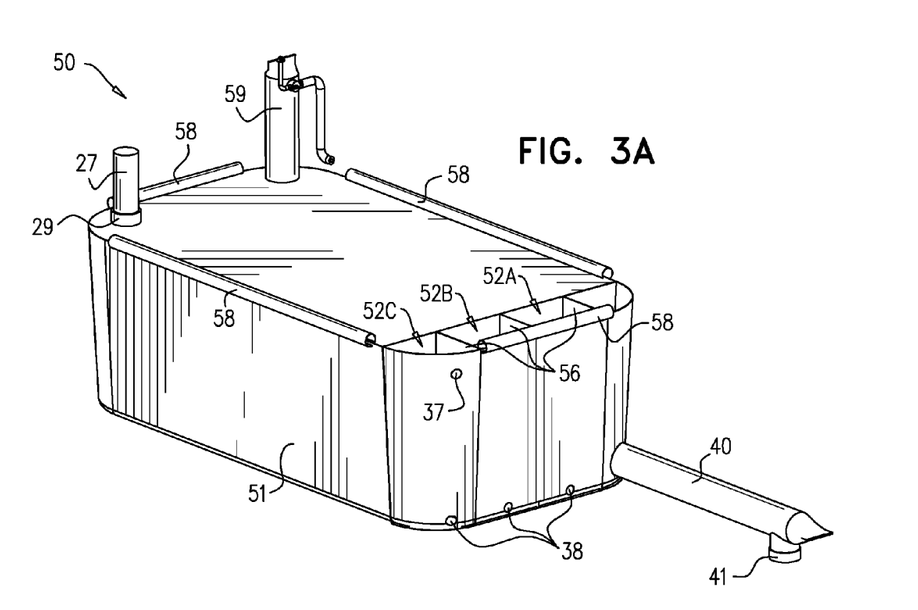
FIG. 3A is an isometric view showing structural details of the anaerobic digester.
Figures 3B, 3C:
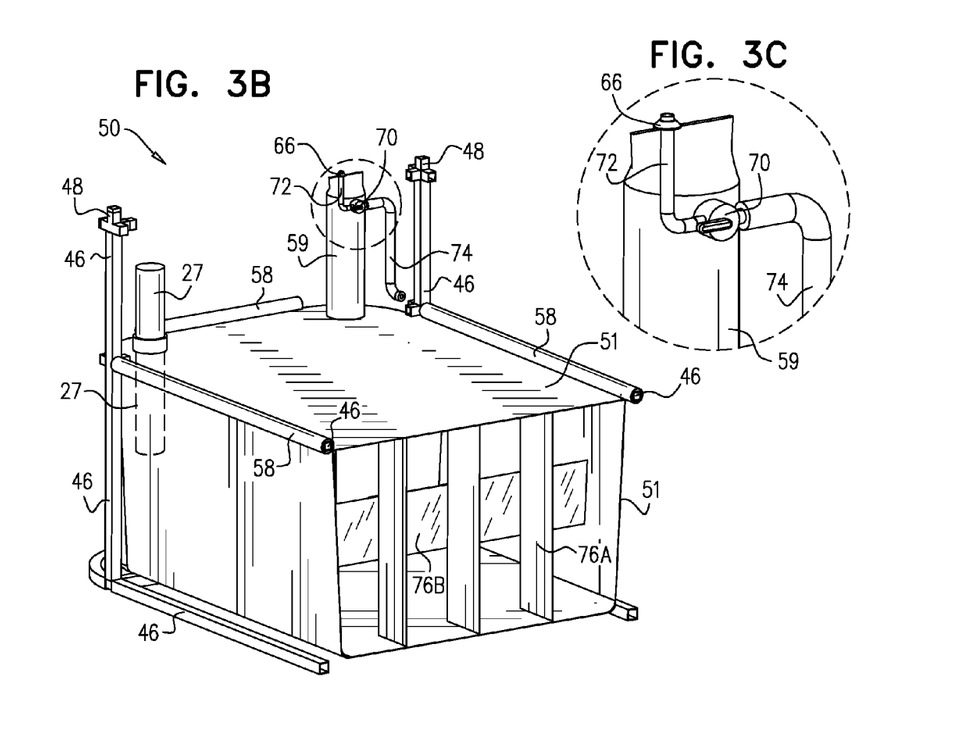
FIG. 3B is an isometric cross-sectional view of the anaerobic digester suspended from the structural scaffolding as well as of interior structural details of the former.
FIG. 3C is an enlarged isometric view of the gas supply assembly, shown in FIG. 3B.

Inlet pipe 27, shown in FIG. 3A-B, employed for feeding the semiliquid mixture or slurry of ground organic matter and fluid into anaerobic digester 50 is hermetically attached to anaerobic digester 50, so that the interior lumen of inlet pipe 27 forming a continuum with interior lumen of anaerobic digester 50. Inlet pipe 27 preferably extends at least through a substantial portion of vertical dimension of anaerobic digester 50.

In an embodiment, multiple structural elements (not shown), such as flanges or pipe fittings, are attached to anaerobic digester 50 surfaces. In one embodiment, at least one inlet pipe 27 and or at least one slurry overflow outlet pipe 34 is/are connected to anaerobic digester 50 with such structural elements (not shown). In an embodiment, gas outlet pipe 59 is connected to anaerobic digester 50 with a structural member. In an embodiment, at least one sludge outlet pipe 40 is connected to anaerobic digester 50 with such a structural element.

It is noted that the anaerobic digestion processes occurring in pliable anaerobic digester 50 resulting a positive pressure therein, mainly of methane gas. Therefore a dedicated means is employed for feeding the aforementioned semiliquid mixture or slurry of ground organic matter and fluid into digester 50 under pressure. Various means are contemplated for accomplishing an effective feeding-in of the aforementioned semiliquid mixture or slurry of ground organic matter and fluid under pressure via inlet pipe 27, while preventing a backflow of gaseous or liquid contents out from anaerobic digester 50, in a non-limiting manner include: a screw pump, a piston manipulated by handle 26 or unidirectional valve disposed in inlet pipe 27.

In some preferred embodiments a piston manipulated by handle 26 includes a circumferential mitral skirt-like element, facilitating essentially unidirectional displacement of the aforementioned semiliquid mixture or slurry of ground organic matter and fluid relatively to the piston. In some preferred embodiments a handle 26 includes a floatation element (not shown) essentially lighter than the aforementioned semiliquid mixture or slurry of ground organic matter, thereby spontaneously driving handle 26 in an upward direction. In some preferred embodiments a handle 26 further includes a plug (not shown), adapted for purposefully sealing the output of sink 24, while handle 26 is in a downward position; thereby providing for thwarting back-flow leakage of the gas from anaerobic digester 50 as well as for controllably preventing advancement of the aforementioned semiliquid mixture or slurry of ground organic matter into inlet pipe 27 and allowing an aerobic pretreatment of aforementioned semiliquid mixture sink 24 for a predefined period of time.

In one embodiment, inlet pipe 27 is connected to a sidewall of anaerobic digester 50, such that the opening in the wall of anaerobic digester 50 is below the midline of the height of anaerobic digester 50.

As shown particularly in FIGS. 1B and 1D, system 10 comprises posterior portion 16, which includes posterior compartment 32. Posterior compartment 32 preferably forms an integral part of pliable collapsible anaerobic digester 50; however posterior compartment 32 optionally forms an individual part, attached to anaerobic digester 50. Posterior compartment 32 is optionally divided by partitions 56, into sub-compartments 52A, 52B and 52C. In one embodiment, apertures 54 in partitions 56 interconnect between sub-compartments 52A to 52C.

Sub-compartments 52A to 52C shown in 1B and 1D are adapted to encompass overflow of liquid fertilizer or slurry resulting the digestion processes in anaerobic digester 50. Liquid fertilizer or slurry is optionally spilled over, from slurry overflow outlet pipe 34, which preferably embodies a siphon configuration, extending from a sidewall of anaerobic digester 50 into sub-compartment 52A. Sub-compartments 52A to 52C, which are exposed to the ambient environment, are adapted to accommodate particular types of plants and microorganisms that function as a biofilter. In one embodiment, the particular types of plants and micro organisms that are capable of reducing sulfur compounds in liquid fertilizer or slurry resulting the digestion processes in anaerobic digester 50; thereby preventing a notorious odor. Sub-compartment 52C optionally includes overflow outlet flange or pipe fitting 37, which is optionally further furnished with nozzle 36, adapted to controllably spill over any excessive liquid fertilizer or slurry resulting the digestion processes from sub-compartment 52C. Sub-compartments 52A to 52C are optionally furnished with sealable drainage apertures 38, adapted to allow conveniently emptying sub-compartments 52A to 52C upon opening of drainage apertures 38. In some embodiments however there is at least one compartment such as 52A that functions as the biofilter.

Posterior portion 16 further includes a sludge outlet draining pipe 40, shown in 1B and 1D, extending from a bottom portion of a sidewall of anaerobic digester 50, adapted for drainage of sludge and/or slurry resulting the digestion processes in anaerobic digester 50. Sludge outlet draining pipe 40 is preferably furnished with sealable cap or baffle 41, adapted for controllably opening/resealing sludge outlet draining pipe 40. Sludge outlet draining pipe 40 is preferably pliable, allowing elevating the terminal portion thereof, thereby preventing the flow from anaerobic digester 50.

Figure 2A:
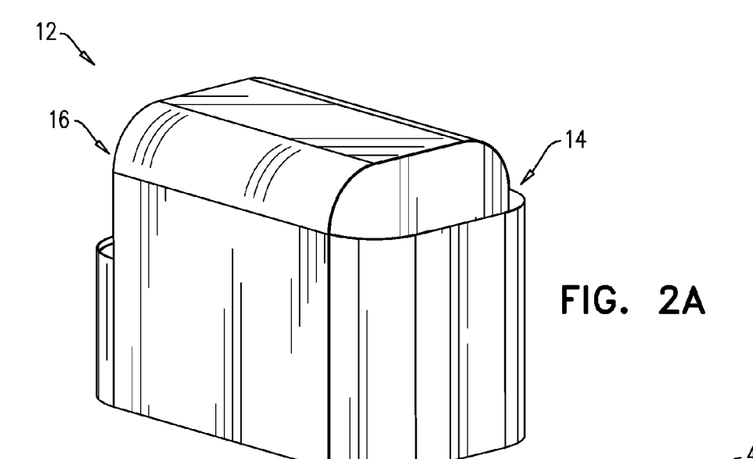
FIG. 2A is an isometric view of the exterior enclosure of a preferred embodiment of the system.
Figures 2B, 2C:
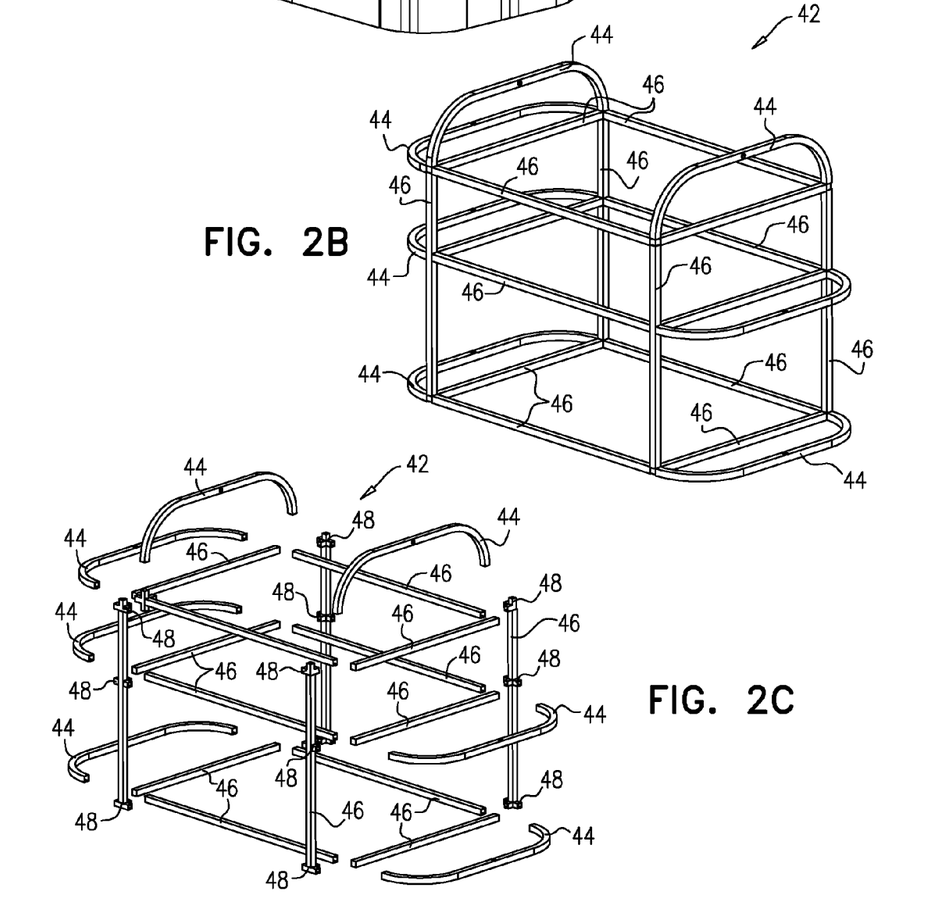
FIG. 2B is an isometric view of the structural scaffolding of a preferred embodiment of the system, in an assembled conformation.
FIG. 2C is an isometric exploded view of the structural scaffolding, in a disassembled conformation.

System 10 comprises assemblable structural scaffolding 42 shown in 2B and 2C. Structural scaffolding 42 comprises a plurality of arcuate structural members 44 and a plurality of linear structural members 46, such as profiles, interconnected by connectors 48. Structural scaffolding 42 is assemblable from a compact kit-of-parts comprising arcuate structural members 44, linear structural members 46 and connectors 48. Structural scaffolding 42 is characterized by a relatively light weight, as well as by compactness of the kit-of-parts used for assembling it; thereby rendering assemblable appliance 10 suitable for shipment and transportation in a rather compact disassembled form. Structural scaffolding 42 comprises at least one structural member configured for suspending pliable collapsible anaerobic digester 50, as elaborated infra.

In one example, connectors 48 are embodied within terminal portions of structural members 44 and 46 and comprise an integral part of structural members 44 and 46. Structural members 44 and 46 thus interlock within each other, for instance by female and male endings of members 44 and 46; whereby multiple parts are connectable directly, without employing any individual connector 48 parts. In one embodiment, structural members 44 and 46 are profiles designed to provide increased bending strength. In one embodiment a couple of linear structural members 46 are provided as a singular L-shaped member. In another embodiment structural members form a closed shape such as a rectangle or ellipse.

Referring particularly to FIG. 3A-B, anaerobic digester 50 is preferably made of at least one sheet of pliable material 51, defining an essentially closed structure; thereby rendering anaerobic digester 50 pliable and collapsible. It is emphasized that aforesaid essentially closed structure includes any pliable and collapsible closed geometrical shapes, in a non-limiting manner including: rectangular, cubical, cylindrical, discoid and globular or spherical closed structures, constitutes a legitimate variation of the pliable and collapsible anaerobic digester 50.

Anaerobic digester 50 shown in FIG. 3A-B is preferably manufactured by welding of polymeric sheets. Therefore anaerobic digester 50 is capable of assuming a collapsed or folded conformation, suitable for shipment and transportation in a rather compact folded form. In other embodiments, however, anaerobic digester 50 is manufactured by welding and/or gluing segments polymeric sheets. In other embodiments, however, anaerobic digester 50 is manufactured by a means of molding, such as vacuum molding or blow molding.

Pliable collapsible anaerobic digester 50 shown in FIG. 3A-B comprises elongated suspension tabs 58 attached along edges of anaerobic digester 50 surfaces. In one embodiment, elongated suspension tabs 58 are attached to the surfaces of anaerobic digester 50. In another embodiment, structural members 46 are threaded into elongated suspension tabs 58, thereby rendering anaerobic digester 50 suspendable from structural scaffolding 42. It is further noted that upon filling anaerobic digester 50 with the aforementioned semiliquid mixture or slurry of ground organic matter and fluid, while anaerobic digester 50 is suspended from structural scaffolding 42, stability is conferred to the structure of assemblable appliance 10 by the gravitational force exerted onto structural members 46 of scaffolding 42.

It is noted that the suspension tabs, such as tabs 58 shown in FIG. 3A-B, potentially embody a variety of shapes and/or structures as well as optionally include additional elements. The suspension tabs, such as tabs 58 optionally form an integral part of pliable collapsible anaerobic digester 50. Suspension tabs, as referred to herein, in a non-limiting manner include: a ring, an elongated sleeve, an abutment for attachment of another element, an element resembling a lifting ear.

In some embodiments, anaerobic digester 50 is suspended by straps and/or harness-like flexible structure (not shown), which are connected to structural scaffolding 42. In yet another embodiment, tab 58 comprises an extension of anaerobic digester 50 threaded into a slot in structural members 46.

Pliable collapsible anaerobic digester 50 shown in FIG. 3A-B further comprises gas outlet pipe 59, hermetically attached to an upper face of digester 50 and extending upwardly therefrom. Baffle 70 is connected to gas outlet pipe 59, for controlling distribution of gas accumulated under positive pressure in pliable anaerobic digester 50 as a result of anaerobic digestion processes occurring therein. Preferably the gas distribution system comprises safety valve 66, coupled to gas outlet pipe 59 and/or baffle 70 by conduit 72. Safety valve 66 is employed to release any excessive pressure of gas from anaerobic digester 50, upon exceeding a predetermined threshold. Gas distribution system further comprises conduit 74, coupling gas tank 60 to gas outlet pipe 59 and/or baffle 70.

In some preferred embodiments, pliable collapsible anaerobic digester 50 comprises a plurality of tension struts, extending between surfaces of said essentially closed structure. In one embodiment, the tension struts are vertical and/or horizontal tension struts 76A and 76B, shown in FIG. 3A-B, extending in-between opposite walls or faces of anaerobic digester 50. Vertical and/or horizontal tension struts 76A and 76B are adapted to prevent excessive deformation or overstretching of anaerobic digester 50 upon buildup of gas pressure therein. In some embodiments, the struts are made from straps of pliable material.

In some preferred embodiments the tension struts as well as optionally the interior surface of the sidewalls of anaerobic digester 50 are furnished with a plurality of minute support structures, such as hair, fins or protrusions used to increase the interior surface area of anaerobic digester 50. The increase in surface area improves the distribution of bacteria throughout the fluid in digester 50. Bacteria have a tendency to sink, over time, to the lower fractions of the digester. The digester typically includes mechanisms used to stir the content fluid so that the bacteria rises and is more uniformly distributed throughout digester 50. The addition to the surface area on the tension struts as well as optionally on internal walls of digester 50 postpones such sinking and thus renders the bacteria more productive.

Figure 5:
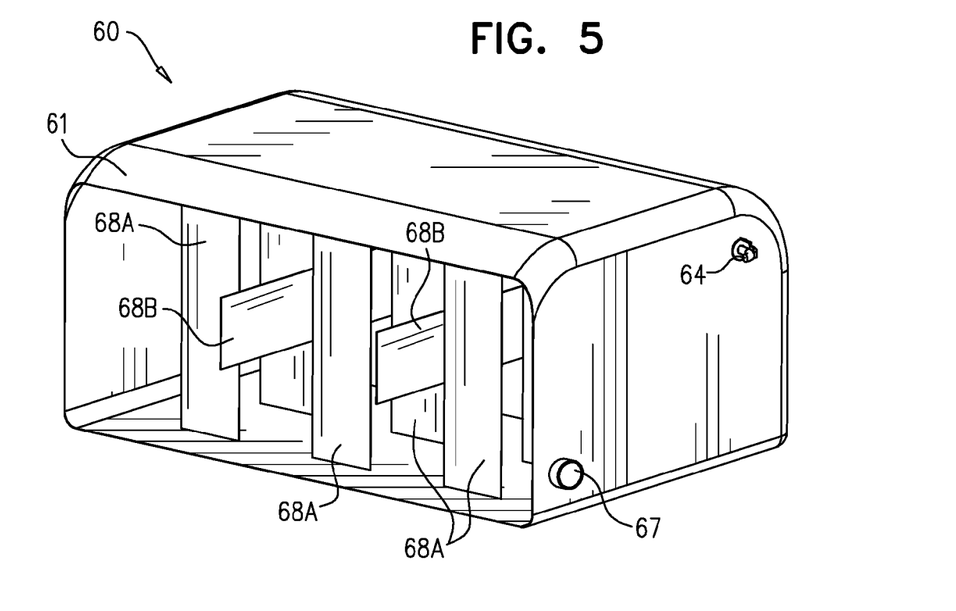
FIG. 5 is an isometric cross-sectional view showing structural details of the resilient gas tank.

Referring particularly to FIG. 5, system 10 comprises a resilient gas tank or bladder 60, employed to accumulate the gas produced by the anaerobic digestion processes tacking place in anaerobic digester 50 under positive pressure for subsequent use. Pliable gas tank 60 is typically disposed on top of anaerobic digester 50. In one embodiment, resilient gas tank 60 is detached from the structural scaffolding 42 while being connected to anaerobic digester 50 with a gas pipe 74. Resilient gas tank 60 is preferably made of at least one sheet of pliable and somewhat resilient material 61, defining an essentially closed structure; thereby rendering gas tank 60 collapsible as well as expandable or stretchable. Therefore pliable gas tank 60 capable of assuming a collapsed or depleted conformation, suitable for shipment and transportation in a rather compact folded form.

It is noted that resilient gas tank 60 shown in FIG. 5 can assume a variety of shapes, inter alia cylindrical, semi-cylindrical and a somewhat rectangular shape, optionally having at least a convex upper face. Resilient gas tank 60 comprises inlet 67 coupled by conduit 74 to the gas distribution system. Resilient gas tank 60 further optionally comprises gas outlet faucet 64, adapted to allow conveniently utilizing the gas. In one embodiment, there is at least one gas flange or gas pipe fitting structural element attached to resilient gas tank 60 surfaces. In some embodiments at least one inlet 67 and or at least one gas outlet valve 64 is connected to resilient gas tank 60 with a structural member.

In some preferred embodiments, resilient gas tank 60 shown in FIG. 5 comprises a plurality of tension struts, extending between surfaces of said essentially closed structure. Wherein the tension struts are adapted to prevent excessive deformation or overstretching of pliable gas tank 60 upon buildup of gas pressure therein. In one embodiment, the tension struts are vertical and/or horizontal tension struts 68A and 68B, respectively, extending in-between opposite walls or faces of pliable gas tank 60.

Figure 4:
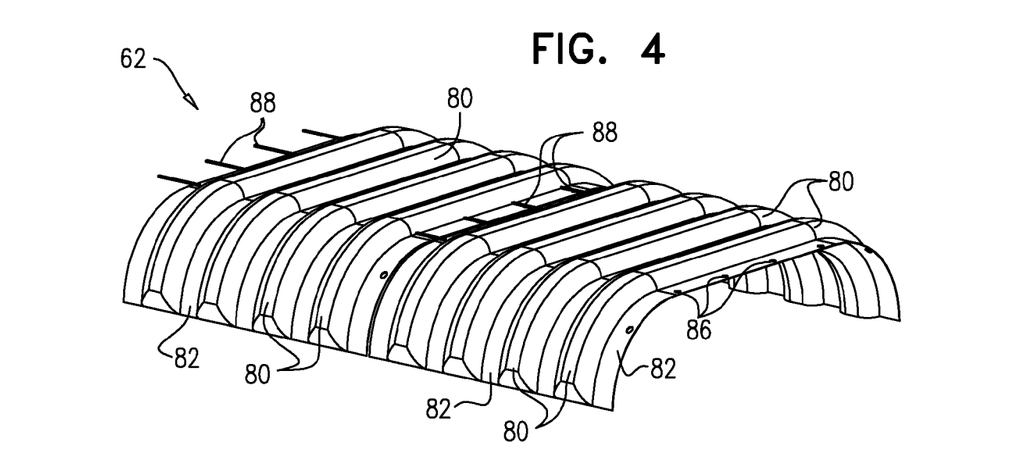
FIG. 4 is an isometric view of the ballast bags for a pliable gas tank.

Referring particularly to FIG. 4, system 10 comprises array 62 of foldable ballast bags 80. Array 62 of ballast bags 80 is employed to exert gravitational force onto a surface of resilient gas tank 60, thereby contributing to the positive pressure of the gas inside gas tank 60 and rendering the gas inside gas tank 60 readily available for utilization. Ballast bags 80 are fillable with ballast substance, typically having a relatively high density or weight to volume ratio, such as sand. In an embodiment, an array 62 of ballast bags 80 is capable of assuming an arcuate conformation, respectively conforming the surface of resilient gas tank 60. In one embodiment, array 62 of ballast bags 80 is capable of assuming a conformation, respectively conforming the shape of the top surface of pliable gas tank 60

In one embodiment, ballast bags 80 shown in FIG. 5 are disposed on foldable bands 82, which are optionally include apertures 86 along the edges thereof. Interconnecting strips 88 are threaded into apertures 86 to adjoin a plurality of foldable bands 82 in tandem. Fillable ballast bags 80 of array 62 are capable of assuming a depleted conformation, suitable for shipment and transportation in a rather compact folded form. In some embodiment array 62 of ballast bags 80 is connected and/or forms an integral part of resilient gas tank 60.

Figure 6A:
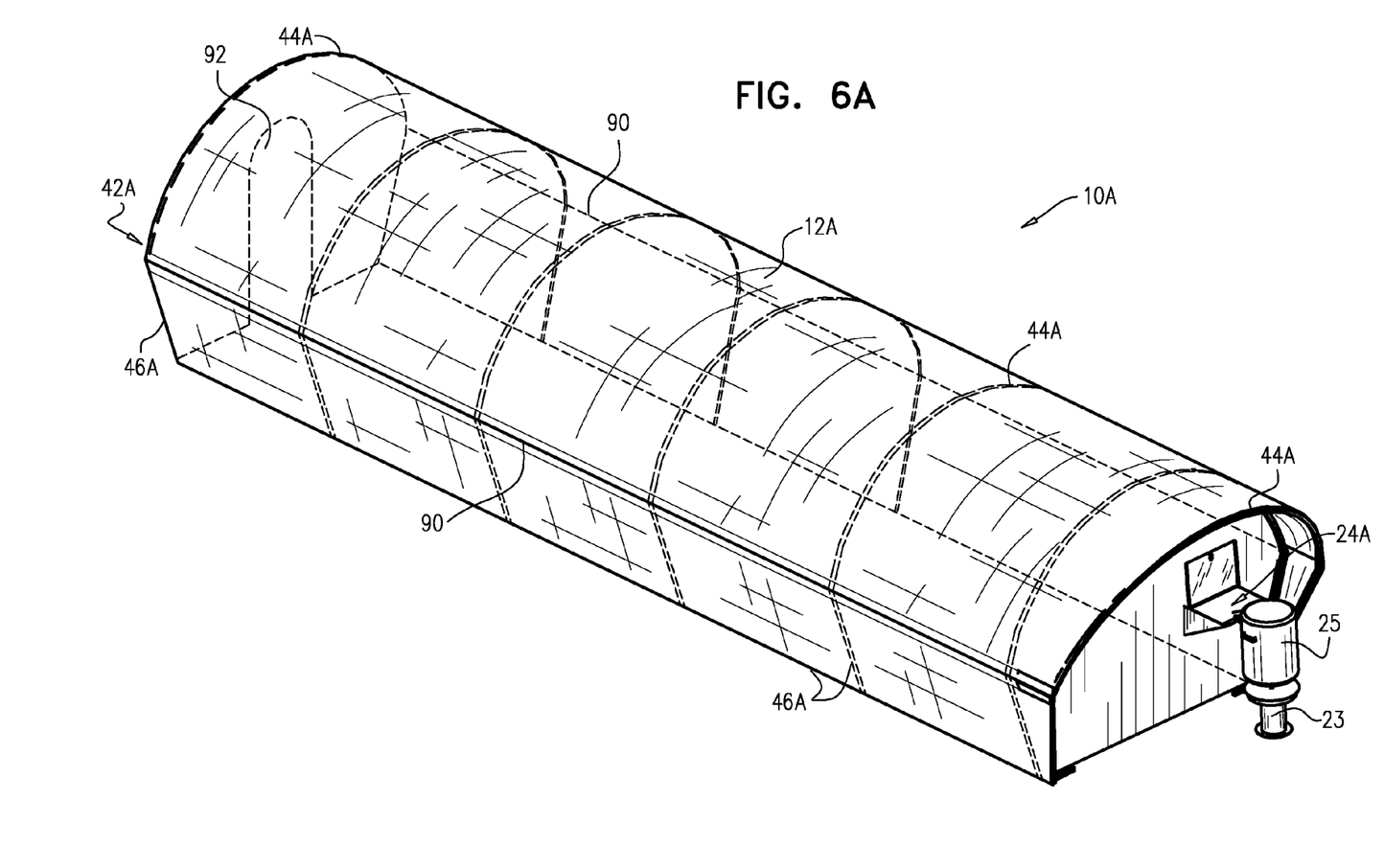
FIG. 6A is a front perspective view of another preferred embodiment of the system, adapted for production of biogas and liquid fertilizer on institutional scale.
Figure 6B:
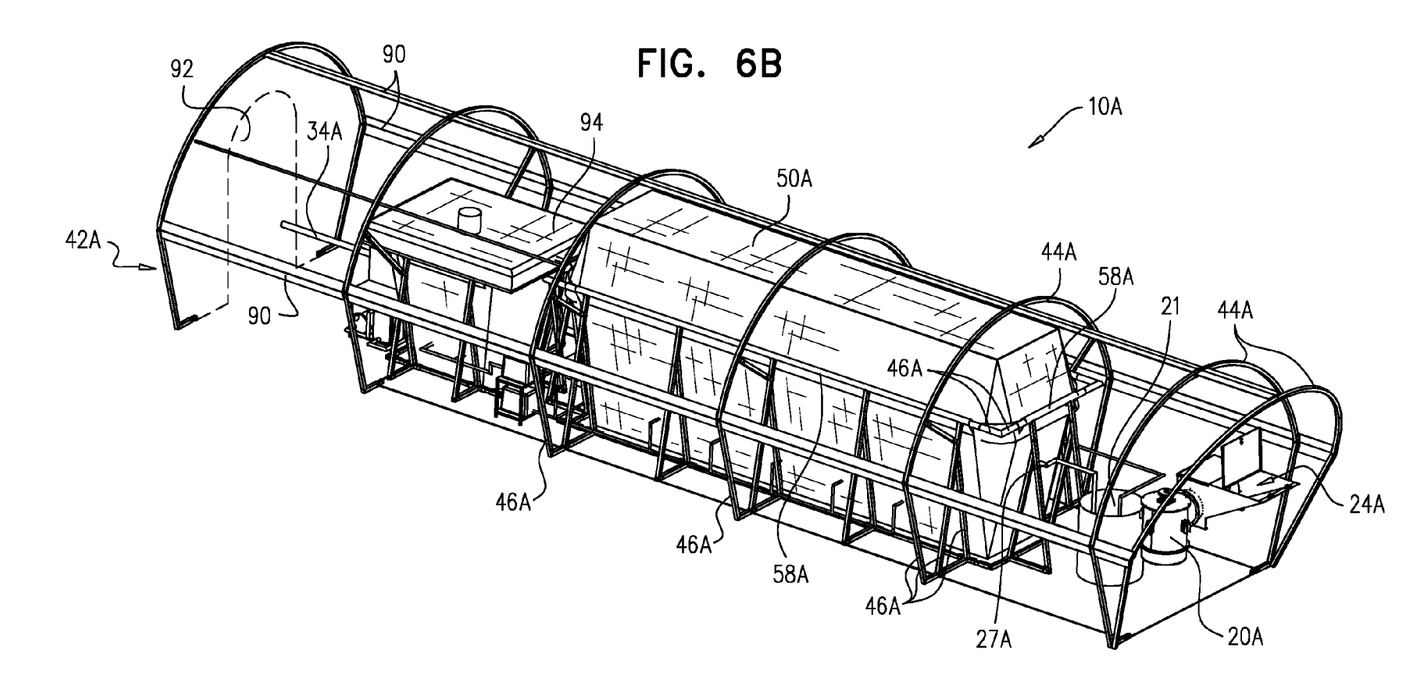
FIG. 6B is a front perspective view of another preferred embodiment of the system of institutional scale, without the exterior enclosure, showing the interior components thereof.

In other preferred embodiments system 10A, shown in FIGS. 6A and 6B, to which reference is now made, utilized for recycling organic waste into biogas and liquid fertilizer on a larger scale. System 10A is utilized in institutional or industrial applications. Recycling organic waste on an institutional or industrial scale entails the capacity of recycling up to hundreds of kilograms of organic waste per day. System 10A, shown in FIGS. 6A and 6B, is typically connected to the institutional infrastructure, such as sewage, electricity as well as water and/or gas distribution pipe systems. In a preferred embodiment system 10A is assemblable with a minimal set of hand tools. In an yet another preferred embodiment system 10A is assemblable by hand.

System 10A, shown in FIGS. 6A and 6B, is adapted for recycling waste on institutional scale, is covered by exterior enclosure 12A. In an embodiment, exterior enclosure 12A comprises a transparent or translucent material, adapted to sustain a greenhouse effect, by capturing some of the solar energy. In an embodiment, exterior enclosure 12A comprises a thermal insulating material. Since system 10A employs essentially anaerobic and non-exothermic digestion processes, an external source of heat is preferably employed for sustaining an effective and fluent continuation of the anaerobic digestion processes, facilitated inter alia by the greenhouse effect of exterior enclosure 12A. In some preferred embodiments exterior enclosure 12A comprising at least one detachable portion (not shown), allowing easy repair or replacement of an individual portion or segment of enclosure 12A.

System 10A shown in FIGS. 6A and 6B includes an anterior portion, accommodating a feeding sub-assembly comprising sink 24A, grinder 20A and aerobic pre-treatment tank 21, as well as a fluid supply (not shown). Feeding sub-assembly optionally further comprises an organic waste dumper container 25, used to accumulate the organic waste throughout the day and scale weight 23, employed to evaluate the weight of organic waste in dumper container 25. Grinder 20A is typically driven by a motor (not shown) connected to a power source and optionally includes a screw pump for conveying the organic waste from sink 24A, into grinder 20A.

The aforementioned feeding sub-assembly is employed for processing an organic waste into a semiliquid mixture or slurry of ground organic matter and fluid, by grinding the organic waste (e.g. by grinder 20A) and mixing the ground organic matter with fluid. The semiliquid mixture or slurry of ground organic matter and fluid is then preferably subjected to an aerobic pretreatment, for about 24 hours, prior to been fed into pliable collapsible anaerobic digester 50A through inlet pipe 27A, which is connected to the outlet of aerobic pre-treatment tank 21.

System 10A shown in FIGS. 6A and 6B comprises structural scaffolding 42A. Structural scaffolding 42A comprises a plurality of arcuate structural members 44A and a plurality of linear structural members 46A, interconnected by connectors (not shown). Structural scaffolding 42A is preferably assembled by affixing a plurality of arco-linear frames, typically comprising at least one arcuate structural member 44A and several linear structural members 46A of different lengths, in tandem along longitudinal beams 90. Longitudinal beams 90 are optionally modular or assemblable from segments.

Structural scaffolding 42A is assemblable from a compact kit-of-parts comprising arcuate structural members 44A, linear structural members 46A as well as optionally connectors (not shown) and/or longitudinal beams 90. Structural scaffolding 42 is characterized by a relatively light weight and by compactness of the kit-of-parts used for assembling the same; thereby rendering system 10A suitable for shipment and transportation in a rather compact disassembled form, frequently requiring less than a single marine shipment payload container.

Structural scaffolding 42A shown in FIGS. 6A and 6B comprises at least one structural member adapted for suspending pliable collapsible anaerobic digester 50A, as elaborated infra. Structural scaffolding 42A of system 10A preferably comprises the components for constructing a terminal arco-linear frame, embodying the shape of doorjamb 92. Doorjamb 92 disposed in terminal posterior arco-linear frame structural scaffolding 42A is used for mounting a door (not shown) allowing a controllably closable walking-through access into the posterior portion of system 10A.

System 10A shown in FIGS. 6A and 6B comprises anaerobic digester 50A which is preferably made of a sheet of pliable material, defining an essentially closed structure: thereby rendering anaerobic digester 504 pliable and collapsible. Anaerobic digester 50A is preferably manufactured by welding of polymeric sheets, however, in some instances anaerobic digester 50A is manufactured by welding and/or gluing segments polymeric sheets or by a means of molding, such as vacuum molding or blow molding. Anaerobic digester 50A is capable of assuming a collapsed or folded conformation, suitable for shipment and transportation in a rather compact folded form. It is once again emphasized that aforesaid essentially closed structure is merely exemplary, whereas any pliable and collapsible closed geometrical shapes, in a non-limiting manner including cylindrical, discoid and globular or spherical closed structures, constitutes a legitimate variation of the pliable and collapsible anaerobic digester 50.

Pliable collapsible anaerobic digester 50A shown in FIGS. 6A and 6B comprises elongated suspension tabs 58A attached along edges of anaerobic digester 50A. Structural members 46A are threaded into elongated suspension tabs 58A, thereby rendering anaerobic digester 50A suspendable from structural scaffolding 42A. It is further noted that upon filling anaerobic digester 50A with the aforementioned semi-liquid mixture or slurry of ground organic matter and fluid, while anaerobic digester 50A is suspended from structural scaffolding 42A, stability is conferred to the structure of system 10A by the gravitational force exerted onto structural members 46A of scaffolding 42A.

It is noted that the suspension tabs, such as tabs 58A shown in FIG. 6B, potentially embody a variety of shapes and/or structures as well as optionally include additional elements. The suspension tabs, such as tabs 58A optionally form an integral part of pliable collapsible anaerobic digester 50A. Suspension tabs, as referred to herein, in a non-limiting manner include: a ring, an elongated sleeve, an abutment for attachment of another element, an element resembling a lifting ear. In some embodiments, anaerobic digester 50 is suspended by straps and/or harness-like flexible structure, which are connected to structural of scaffolding 42. In yet another embodiment, tab 58 comprises an extension of anaerobic digester 50 threaded into a slot in structural members 46.

Posterior portion of assemblable appliance 10A, at the rear of anaerobic digester 50A, comprises aerobic biofilter 94 shown in FIG. 6B. Biofilter 94 is a scaled-up embodiment of posterior compartment 32 of system 10 shown in FIG. 1A-D, adapted to encompass overflow of liquid fertilizer or slurry resulting the digestion processes in anaerobic digester 50A. Liquid fertilizer or slurry is optionally supplied into biofilter 94, by a slurry overflow outlet pipe, extending from a sidewall of anaerobic digester 50A. Biofilter 94 is typically supplied with air for the ambient environment and adapted to accommodate particular types of microorganisms and or plants. In an embodiment the microorganisms and or plants are capable of reducing sulfur compounds in liquid fertilizer or slurry resulting the digestion processes in anaerobic digester 50A; thereby preventing a notorious odor. The liquid fertilizer or slurry is output from biofilter 94 via slurry outlet pipe 34A.

System 10A shown in FIG. 6B further comprises a gas outlet pipe, hermetically attached to an upper portion of anaerobic digester 50A and a sludge outlet draining pipe, extending from a bottom portion thereof. The gas outlet pipe is typically connected to a compressor, supplying compressed biogas into the institutional distribution system; whereas the sludge outlet draining pipe is typically connected to the institutional sewage. System 10A optionally includes a pipe system and/or manifold, disposed at the bottom portion of digester 50A, used to recirculate a portion of the biogas throughout anaerobic digester 50A thereby stirring up the contents thereof.

Figure 7A:
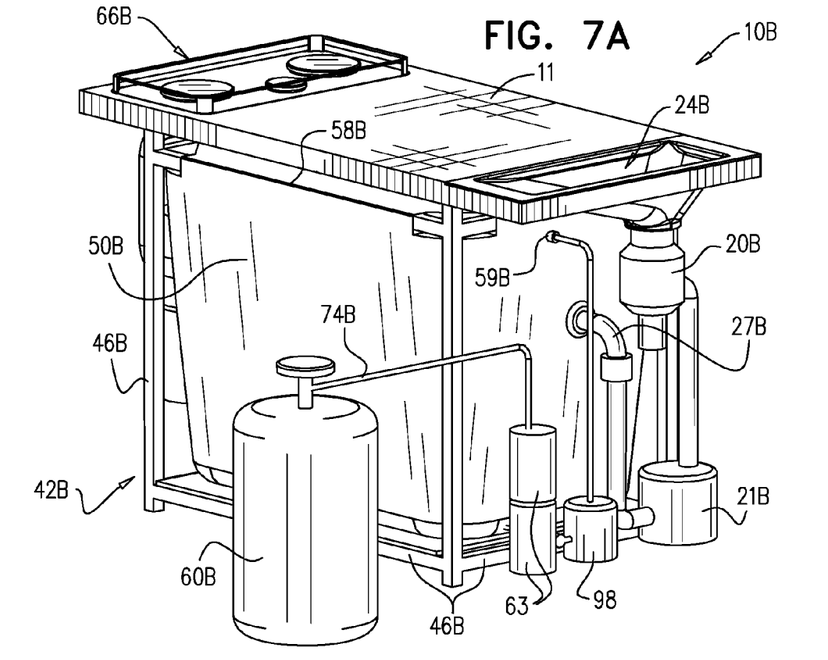
FIG. 7A is a front perspective view of yet another preferred embodiment of the assemblable appliance, adapted for being built into a domestic kitchen.
Figure 7B:
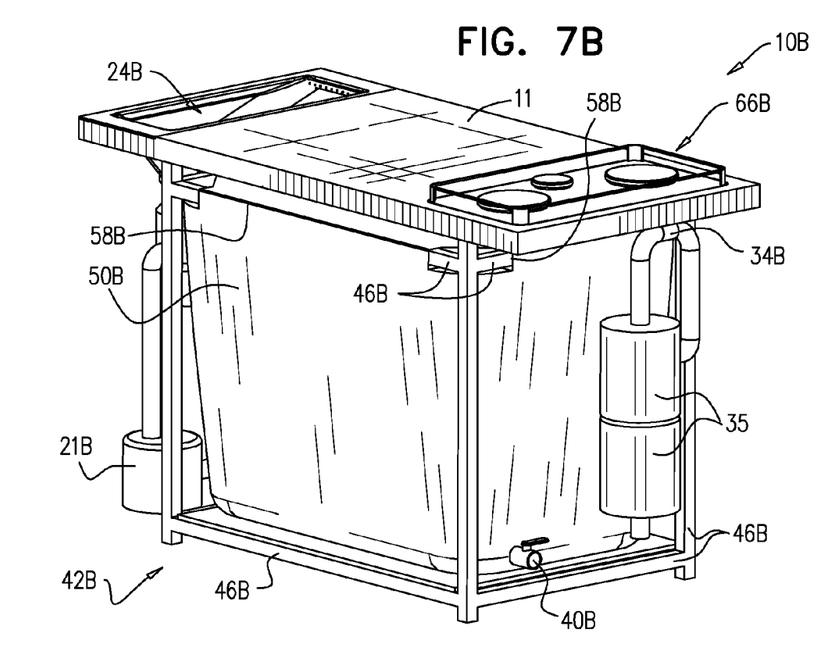
FIG. 7B is a back perspective view of the embodiment of the assemblable appliance, adapted for being built into a domestic kitchen.

In other preferred embodiments assemblable appliance 10B, shown in FIGS. 7A and 7B, to which reference is now made, is adapted for been built into standard domestic kitchen. Assemblable appliance 10B, shown in FIGS. 7A and 7B, adapted for been built into or form a part of a standard domestic kitchen, is typically connected to the domestic infrastructure, such as sewage, electricity as well as water and/or gas distribution pipe systems.

Assemblable appliance 10B, shown in FIGS. 7A and 7B adapted for been built into a standard domestic kitchen, is typically covered by exterior panels (not shown) which are optimally supplied by the user, so as to fit or form a consistent interior design of the kitchen. In an embodiment an external source of heat is employed for sustaining an effective and fluent continuation of the anaerobic digestion processes, facilitated for instance by a controlled electric heater (not shown).

Assemblable appliance 10B includes working surface 11 shown in FIGS. 7A and 7B, from which organic waste is directly put into the feeding sub-assembly at the anterior portion assemblable appliance 10B, comprising dedicated sink 24B, grinder 20B and sludge pump 21B, as well as a fluid supply (not shown). Grinder 20B is typically a standard domestic garbage disposer driven by an electric motor (not shown) connected to sink 24B. The aforementioned feeding sub-assembly is employed for processing organic waste into a semiliquid mixture or slurry of ground organic matter and fluid, by grinding the organic waste (e.g. by garbage disposer 20B), mixing the ground organic matter with fluid and further feeding the resultant semiliquid mixture or slurry, for instance by sludge pump 21B, via inlet pipe 27B, into anaerobic digester 50B.

Assemblable appliance 10B comprises structural scaffolding 42B shown in FIGS. 7A and 7B which is typically assemblable from a compact kit-of-parts. Structural scaffolding 42B is characterized by a relatively simple construction and hence in some embodiments, structural scaffolding 42B is not assemblable, as referred to herein, but rater built by the installers while constructing the kitchen. Structural scaffolding 42B comprises a plurality of linear structural members 46B, optionally interconnected by connectors (not shown). Structural scaffolding 42B comprises at least one structural member adapted for suspending pliable collapsible anaerobic digester 50B.

Assemblable appliance 10B comprises anaerobic digester 50B shown in FIGS. 7A and 7B which is preferably made of at least one sheet of pliable material, defining an essentially closed structure; thereby rendering anaerobic digester 50A pliable and collapsible. Anaerobic digester 50B is manufactured as set forth hereinabove.

In an embodiment pliable collapsible anaerobic digester 50B comprises elongated suspension tabs 58A attached along edges of anaerobic digester 50B. In an embodiment, elongated suspension tabs 58A are attached on surfaces of anaerobic digester 50B, Structural members 46B are threaded into elongated suspension tabs 58B, thereby rendering anaerobic digester 50B suspendable from structural scaffolding 42B.

It is noted that the suspension tabs, such as tabs 58B shown in FIGS. 7A and 7B, potentially embody a variety of shapes and/or structures as well as optionally include additional elements. The suspension tabs, such as tabs 58B optionally form an integral part of pliable collapsible anaerobic digester 50B. Suspension tabs, as referred to herein, in a non-limiting manner include: a ring, an elongated sleeve, an abutment for attachment of another element, an element resembling a lifting ear.

Posterior portion of assemblable appliance 10B, at the rear of anaerobic digester 50B, comprises filter 35 shown in FIGS. 7A and 7B. Filter 35 is adapted to drain overflow of liquid fertilizer or slurry resulting the digestion processes in anaerobic digester 50B. Liquid fertilizer or slurry is supplied into filter 35, by a slurry overflow outlet pipe 34B, preferably embodying a siphon configuration, extending from a sidewall of anaerobic digester 50B. Filter 35 is typically capable of reducing and/or removing sulfur compounds in liquid fertilizer or slurry resulting the digestion processes in anaerobic digester 50B; thereby preventing odor. The liquid fertilizer or slurry is output from filter 35 via slurry outlet pipe 34B which is optionally connected or connectable to the domestic sewage system.

Assemblable appliance 10B shown in FIGS. 7A and 7B further comprises a gas outlet pipe 59B, hermetically attached to an upper portion of anaerobic digester 50B and a sludge outlet draining pipe 40B, extending from a bottom portion thereof. Gas outlet pipe 59B is typically connected to a compressor 98. Compressor 98, which is typically actuated by a pressure sensor, upon attaining a predetermined level, compresses biogas, pushes compressed biogas through filters and/or dehydrators 63. Thereafter compressed filtered and/or dehydrated biogas is supplied via conduit 74B into gas into domestic gas tank 60B, from which is optionally supplied to burner unit 66B. Sludge outlet draining pipe 40B is typically connected to the domestic sewage system. Assemblable appliance 10B optionally includes a pipe system and/or manifold, disposed at the bottom portion of digester 50A, used to recirculate a portion of the biogas throughout anaerobic digester 50A thereby stirring up the contents thereof.

Wherever in the specification hereinabove and in claims hereunder it is noted that the pliable collapsible anaerobic digester, such as digester 50, including or comprising an inlet pipe, gas outlet pipe, slurry overflow outlet pipe or sludge outlet draining pipe—it should be construed that the pliable collapsible anaerobic digester includes or comprises merely a preparation on the surface thereof and/or inside the wall thereof as well as an additional element for relatively easily mounting and/or attaching an inlet pipe, gas outlet pipe, slurry overflow outlet pipe or sludge outlet draining pipe thereto, whereas the inlet pipe, gas outlet pipe, slurry overflow outlet pipe or sludge outlet draining pipe are not provided or attached to the digester.

It will be appreciated by persons skilled in the art that the present invention is not limited by what has been particularly shown and described herein above. Rather the scope of the invention is defined by the claims which follow:

The invention claimed is:

1. An assemblable appliance for recycling organic waste into biogas and liquid fertilizer, implementing essentially anaerobic digestion processes, said assemblable appliance is operable as an autonomic standalone unit, said assemblable appliance comprises:
   (a) a structural scaffolding, wherein said structural scaffolding is assemblable from a compact kit-of-parts, configured for transportation in a compact form, said structural scaffolding comprising:
      (I) a plurality of structural members;
      (II) a plurality of connectors, configured to interconnect said structural members;
   (b) a pliable collapsible anaerobic digester, said anaerobic digester comprising:
      (I) a sheet of pliable material, forming an essentially closed structure, wherein said structure comprises an essentially rectangular shape;

(II) at least two suspension tabs, attached to said closed structure, thereby rendering said anaerobic digester suspendable from said structural scaffolding; wherein said at least two suspension tabs comprise at least two elongated sleeves; wherein said suspension tabs are attached alongside at least two upper edges of said rectangular shape; wherein said suspension tabs extend along at least a substantial portion of a length of said upper edges of said rectangular shape; and wherein each one of said suspension tabs is configured to receive a linear structural member of said structural scaffolding;

(III) an inlet pipe for feeding a semiliquid mixture of organic matter and water into said anaerobic digester, said inlet pipe is hermetically attached to said anaerobic digester, wherein interior lumen of said inlet pipe forming a continuum with interior lumen of said anaerobic digester;

(IV) a gas outlet pipe, hermetically attached to an upper face of said anaerobic digester and extending upwardly therefrom;

(V) a slurry overflow outlet pipe, extending from a sidewall of said essentially closed structure;

(VI) a sludge outlet draining pipe, extending from a bottom portion of a sidewall of said essentially closed structure;

(c) a collapsible gas tank, said collapsible gas tank comprising:
(I) a sheet of pliable material, forming a closed structure;
(II) at least one element selected from the group consisting of:
(i) a gas inlet, and
(ii) a gas outlet;

(d) at least one flexible elongated and foldable ballast bag, fillable with ballast substance, said flexible elongated ballast bag is capable of assuming a conformation, respectively matching the shape of said collapsible gas tank.

2. The assemblable appliance, as set forth in claim 1, further comprises at least one component, of a feeding sub-assembly, selected from the group consisting of:
(a) a sink, wherein an outlet of said sink is connected to said inlet pipe of said pliable collapsible anaerobic digester;
(b) a grinder; disposed on top of said sink, capable of grinding said organic waste into said semiliquid mixture;
(c) a sink cover, wherein said sink cover is characterized by a sloped or slated shape, thereby facilitating feeding said organic waste into said grinder;
(d) a water canister, disposed on top of said sink, for supplying a water fraction for said semiliquid mixture;
(e) a water tap, connected to said water canister ater supply hose, for controlling the amount of said water fraction in said semiliquid mixture.

3. The assemblable appliance, as set forth in claim 1, further comprises a mechanism configured for feeding said semiliquid mixture under pressure into said inlet pipe of said pliable collapsible anaerobic digester.

4. The assemblable appliance as set forth in claim 3, wherein said mechanism configured for feeding said semiliquid mixture under pressure is selected from the group consisting of: a screw pump, piston with a handle, a unidirectional valve, a piston furnished with circumferential mitral skirt-like element, a floatation element and a plug adapted for sealing said output of said sink.

5. The assemblable appliance, as set forth in claim 1, further comprises an exterior enclosure surrounding said assemblable appliance, said exterior enclosure is capable of sustaining a greenhouse effect, thereby providing for a source of heat for said anaerobic digestion processes.

6. The assemblable appliance as set forth in claim 1, wherein said inlet pipe of said pliable collapsible anaerobic digester extends through an at least substantial portion of vertical dimension of said essentially closed structure of said anaerobic digester.

7. The assemblable appliance as set forth in claim 1, wherein said pliable collapsible anaerobic digester further comprises a plurality of tension straps, extending in-between opposite inward faces of said essentially closed structure of said anaerobic digester.

8. The assemblable appliance as set forth in claim 1, wherein said pliable collapsible anaerobic digester is manufactured by welding of polymeric sheets.

9. The assemblable appliance as set forth in claim 1, wherein said at least two suspension tabs, attached along said at least two upper edges of said rectangular shape further comprise at least one element selected from the group consisting of: a ring, attachment element abutment and lifting ear.

10. The assemblable appliance as set forth in claim 1, wherein said at least two suspension tabs, attached along said at least two upper edges of said essentially closed structure of said anaerobic digester form an integral part of said pliable collapsible anaerobic digester.

11. The assemblable appliance as set forth in claim 1, wherein said gas tank comprises an essentially bladder resembling structure.

12. The assemblable appliance as set forth in claim 1, wherein said slurry outlet pipe further comprises a siphon mechanism, configured to sustain a positive pressure inside said digester.

13. A method of recycling organic waste into biogas and liquid fertilizer, implementing essentially anaerobic digestion processes, by a means of assemblable appliance, said method comprises:
(a) providing a compact kit-of-parts, adapted for transportation in a compact form, said kit-of-parts comprising:
(I) a plurality of structural members;
(II) a plurality of connectors, configured to interconnect said structural members;
(b) assembling a structural scaffolding from said kit-of-parts;
(c) providing a pliable collapsible anaerobic digester, said anaerobic digester comprising:
(I) a sheet of pliable material, forming an essentially closed structure, wherein said structure comprises an essentially rectangular shape;
(II) at least two suspension tabs, attached along at least two upper edges of said rectangular shape, rendering said anaerobic digester suspendable from said structural scaffolding; wherein said at least two suspension tabs comprise at least two elongated sleeves; wherein said suspension tabs extend along at least a substantial portion of a length of said upper edges of said rectangular shape and wherein each one of said suspension tabs is configured to receive a structural member of said structural scaffolding;
(III) an inlet pipe for feeding a semiliquid mixture of organic matter and water into said anaerobic digester, said inlet pipe is hermetically attached to said anaerobic digester, wherein interior lumen of said inlet pipe forming a continuum with interior lumen of said anaerobic digester;
(IV) a gas outlet pipe, hermetically attached to an upper face of said anaerobic digester and extending upwardly therefrom;
(V) a slurry overflow outlet pipe, extending from a sidewall of said essentially closed structure;
(VI) a sludge outlet draining pipe, extending from a bottom portion of a sidewall of said closed structure;
(d) suspending said pliable collapsible anaerobic digester from said structural scaffolding by a means of said suspension tabs;
(e) feeding a semiliquid mixture or slurry of ground organic matter and water into said pliable collapsible anaerobic digester and sustaining an essentially anaerobic digestion processes therein.

14. The method of recycling organic waste, as set forth in claim 13, wherein said assemblable appliance further comprises at least one component, of a feeding sub-assembly, selected from the group consisting of:
(a) a sink, wherein an outlet of said sink is connected to said inlet pipe of said pliable collapsible anaerobic digester;
(b) a grinder; disposed on top of said sink, capable of grinding said organic waste;
(c) a sink cover, wherein said sink cover is characterized by a sloped or slated shape, thereby facilitating feeding said organic waste into said grinder;
(d) a water canister, disposed on top of said sink, for supplying a water fraction for said semiliquid mixture or slurry;
(e) a water tap, connected to said water canister or a water supply hose, for controlling the amount of said water fraction in said semiliquid mixture or slurry.

15. The method of recycling organic waste; as set forth in claim 13, further comprises grinding said organic matter and supplying a water fraction to form said semiliquid mixture or slurry.

16. The method of recycling organic waste, as set forth in claim 13, wherein said assemblable appliance further comprises a mechanism configured for feeding said semiliquid mixture under pressure into said inlet pipe of said pliable collapsible anaerobic digester.

17. The method of recycling organic waste, as set forth in claim 16, wherein said mechanism configured for feeding said semiliquid mixture under pressure is selected from the group consisting of: a screw pump, piston with a handle, a unidirectional valve, a piston furnished with circumferential mitral skirt-like element, a floatation element and a plug adapted for sealing said output of said sink.

18. The method of recycling organic waste, as set forth in claim 13, further comprises providing for an external source of heat for said sustaining said essentially anaerobic digestion processes.

19. The method of recycling organic waste, as set forth in claim 13, wherein said inlet pipe of said pliable collapsible anaerobic digester extends through an at least substantial portion of vertical dimension of said essentially closed structure.

20. The method of recycling organic waste, as set forth in claim 13, wherein said pliable collapsible anaerobic digester further comprises a plurality of tension straps, extending in-between opposite inward faces of said essentially closed structure.

21. The method of recycling organic waste, as set forth in claim 13, wherein said pliable collapsible anaerobic digester is manufactured by welding of polymeric sheets.

22. The method of recycling organic waste, as set forth in claim 13, wherein said at least two suspension tabs, attached along said at least two upper edges of said rectangular shape comprise at least one element selected from the group consisting of: a ring, attachment element abutment, lifting ear.

23. The method of recycling organic waste, as set forth in claim 13, wherein said at least two suspension tabs, attached along said at least two upper edges of said essentially closed structure form an integral part of said pliable collapsible anaerobic digester.

24. The method of recycling organic waste, as set forth in claim 13, further comprises accumulating said biogas under a positive pressure driven by gravitational force.

25. The method of recycling organic waste, as set forth in claim 13, wherein said slurry outlet pipe comprises a siphon mechanism, configured to sustain a positive pressure inside said digester.

26. A compact kit-of-parts, configured for transportation in a compact form, of an assemblable appliance for recycling organic waste into biogas and liquid fertilizer, implementing essentially anaerobic digestion processes, said kit-of-parts comprises:
(a) a plurality of structural members of a structural scaffolding;
(b) a plurality of connectors, configured to interconnect said at structural members:
(c) a pliable collapsible anaerobic digester, said anaerobic digester comprising:
(I) a sheet of pliable material, forming a closed essentially closed structure, wherein said structure comprises an essentially rectangular shape;
(II) at least two suspension tabs, attached along at least two upper edges of said rectangular shape, rendering said anaerobic digester suspendable from said structural scaffolding; wherein said at least two suspension tabs comprise at least two elongated sleeves; wherein said suspension tabs extend along at least a substantial portion of a length of said upper edges of said rectangular shape and wherein each one of said suspension tabs is configured to receive a structural member of said structural scaffolding;
(III) an inlet pipe for feeding a semiliquid mixture of organic matter and water into said anaerobic digester, said inlet pipe is hermetically attached to said anaerobic digester, wherein interior lumen of said inlet pipe forming a continuum with interior lumen of said anaerobic digester;
(IV) a gas outlet pipe; hermetically attached to an upper face of said anaerobic digester and extending upwardly therefrom;
(V) a slurry overflow outlet pipe, extending from a sidewall of said essentially closed structure;
(VI) a sludge outlet draining pipe, extending from a bottom portion of a sidewall of said essentially closed structure;
wherein said pliable collapsible anaerobic digester is suspendable from said structural scaffolding by a means of said suspension tabs.

27. The compact kit-of-parts, as set forth in claim 26, further comprises at least one component, of a feeding sub-assembly, selected from the group consisting of:
(a) a sink, wherein an outlet of said sink is connectable to said inlet pipe of said pliable collapsible anaerobic digester;
(b) a grinder capable of grinding said organic waste into said semiliquid mixture;

(c) a sink cover; wherein said sink cover is characterized by a sloped or slated shape, thereby facilitating feeding said organic waste into said grinder;
(d) a water canister, disposed on top of said sink, for supplying a water fraction for said semiliquid mixture;
(e) a water tap, connected to said water canister or a water supply hose, for controlling the amount of said water fraction in said semiliquid mixture.

28. The compact kit-of-parts, as set forth in claim 26, further comprises a mechanism configured for feeding said semiliquid mixture under pressure into said inlet pipe of said pliable collapsible anaerobic digester.

29. The compact kit-of-parts as set forth in claim 28, wherein said mechanism configured for feeding said semiliquid mixture under pressure is selected from the group consisting of: a screw pump; piston with a handle, a unidirectional valve, a piston furnished with circumferential mitral skirt-like element, a floatation element and a plug adapted for sealing said output of said sink.

30. The compact kit-of-parts as set forth in claim 26, wherein said inlet pipe of said pliable collapsible anaerobic digester extends through an at least substantial portion of vertical dimension of said essentially closed structure.

31. The compact kit-of-parts as set forth in claim 26, wherein said pliable collapsible anaerobic digester further comprises a plurality of tension straps, extending in-between opposite inward faces of said essentially closed structure.

32. The compact kit-of-parts as set forth in claim 26, wherein said at least two suspension tabs, attached along said at least two upper edges of said rectangular shape comprise at least one element selected from the group consisting of: a ring, attachment element abutment and lifting ear.

33. The compact kit-of-parts as set forth in claim 26, wherein said at least two suspension tabs, attached along said at least two upper edges of said essentially closed structure form an integral part of said pliable collapsible anaerobic digester.

34. The compact kit-of-parts, as set forth in claim 26, further comprises a collapsible gas tank.

35. The compact kit-of-parts as set forth in claim 26, further comprises a plurality of flexible ballast bags, fillable with a ballast substance.

36. The compact kit-of-parts as set forth in claim 26, wherein said slurry outlet pipe comprises a siphon mechanism, configured to sustain a positive pressure inside said digester.

* * * * *